US011645888B2

(12) United States Patent
Farooq

(10) Patent No.: US 11,645,888 B2
(45) Date of Patent: *May 9, 2023

(54) ELECTRONIC GAMING SYSTEM AND METHOD OF PROVIDING PROGRESSIVE JACKPOT PLAY

(71) Applicant: Aristocrat Technologies Australia Pty Limited, North Ryde (AU)

(72) Inventor: Raheem Farooq, London (GB)

(73) Assignee: Aristocrat Technologies Australia Pty Limited, North Ryde (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/109,986

(22) Filed: Dec. 2, 2020

(65) Prior Publication Data

US 2021/0121643 A1 Apr. 29, 2021

Related U.S. Application Data

(63) Continuation of application No. 15/237,276, filed on Aug. 15, 2016, now Pat. No. 10,867,476.

(51) Int. Cl.
*G07F 17/32* (2006.01)
*A61M 11/00* (2006.01)
(Continued)

(52) U.S. Cl.
CPC .......... *G07F 17/3258* (2013.01); *A24D 3/08* (2013.01); *A24F 1/30* (2013.01); *A61M 11/003* (2014.02);
(Continued)

(58) Field of Classification Search
CPC ............ G07F 17/3258; G07F 17/3293; G07F 17/3209; G07F 17/3211; G07F 17/3223;
(Continued)

(56) References Cited

U.S. PATENT DOCUMENTS 4,948,134 A * 8/1990 Suttle .................. G07F 17/3293
D21/370
5,022,653 A * 6/1991 Suttle ...................... G07F 17/32
273/274

(Continued)

OTHER PUBLICATIONS

Office Action dated May 20, 2020 for U.S. Appl. No. 15/237,276 (pp. 1-14).
(Continued)

*Primary Examiner* — Malina D. Blaise
(74) *Attorney, Agent, or Firm* — Armstrong Teasdale LLP

(57) ABSTRACT

A gaming system is provided, including a jackpot server and a gaming server. The jackpot server accumulates respective contributions from gaming client devices into a progressive jackpot. The gaming server presents wagering games to a player on a gaming client device. The wagering games include a first wagering game having a progressive jackpot component, and a second wagering game not having a progressive jackpot component. The gaming server receives a jackpot token from the player, including a token identification associated with the player and a progressive jackpot identification correlating to a token progressive jackpot. A wager is received for the second wagering game, which is conducted such that the player participates in the token progressive jackpot. The gaming server transmits a message to the jackpot server, including a portion of the wager as a contribution to the token progressive jackpot and an outcome of the second wagering game.

20 Claims, 6 Drawing Sheets

(51) Int. Cl.
*A61M 11/04* (2006.01)
*A24D 3/08* (2006.01)
*A24F 1/30* (2006.01)
*A61M 15/00* (2006.01)

(52) U.S. Cl.
CPC ....... *A61M 11/048* (2014.02); *G07F 17/3209* (2013.01); *G07F 17/3211* (2013.01); *G07F 17/3223* (2013.01); *G07F 17/3225* (2013.01); *G07F 17/3244* (2013.01); *G07F 17/3269* (2013.01); *G07F 17/3272* (2013.01); *A61M 15/0021* (2014.02); *A61M 2205/11* (2013.01); *A61M 2205/7545* (2013.01)

(58) Field of Classification Search
CPC ............. G07F 17/3225; G07F 17/3244; G07F 17/3269; G07F 17/3272
See application file for complete search history.

(56) References Cited

U.S. PATENT DOCUMENTS

| | | | | |
|---|---|---|---|---|
| 5,377,973 | A * | 1/1995 | Jones | A63F 3/00157 463/13 |
| 5,573,248 | A * | 11/1996 | Parra | A63F 9/0406 273/274 |
| 5,951,011 | A * | 9/1999 | Potter | A63F 3/00157 463/13 |
| 6,629,591 | B1 * | 10/2003 | Griswold | G07F 1/06 463/25 |
| 7,303,475 | B2 | 12/2007 | Britt | |
| 7,922,176 | B1 | 4/2011 | Kelly | |
| 9,251,647 | B2 | 2/2016 | Nelson | |
| 9,349,244 | B2 | 5/2016 | Weingardt | |
| 2001/0031659 | A1 | 10/2001 | Perrie | |
| 2003/0069071 | A1 | 4/2003 | Britt | |
| 2003/0204738 | A1 * | 10/2003 | Morgan | H04L 63/0853 713/194 |
| 2005/0167912 | A1 * | 8/2005 | Sokolov | G07F 17/3213 273/143 R |
| 2005/0251440 | A1 * | 11/2005 | Bednarek | G06Q 30/0601 705/7.32 |
| 2006/0052169 | A1 | 3/2006 | Britt | |
| 2006/0142086 | A1 | 6/2006 | Blackburn | |
| 2007/0060321 | A1 * | 3/2007 | Vasquez | G07F 17/32 463/27 |
| 2007/0191088 | A1 * | 8/2007 | Breckner | G07F 17/3258 463/20 |
| 2007/0265066 | A1 * | 11/2007 | Curry | G07F 17/3258 463/26 |
| 2008/0045346 | A1 | 2/2008 | Nelson | |
| 2008/0188296 | A1 | 8/2008 | Seelig | |
| 2008/0261699 | A1 | 10/2008 | Topham | |
| 2009/0054134 | A1 * | 2/2009 | Jackson | G07F 17/3258 463/25 |
| 2009/0275404 | A1 * | 11/2009 | Kromydas | G07F 17/3262 463/29 |
| 2011/0183762 | A1 | 7/2011 | Topham | |
| 2013/0173658 | A1 * | 7/2013 | Adelman | H04L 63/0492 707/769 |
| 2016/0086450 | A1 | 3/2016 | Lyons | |
| 2016/0148460 | A1 | 5/2016 | Nelson | |

OTHER PUBLICATIONS

Australian Examination Report No. 1 for Application No. AU2019201631, dated Feb. 27, 2020, 3 pages.
Notice of Allowance dated Nov. 2, 2020 for U.S. Appl. No. 15/237,276 (pp. 1-9).

* cited by examiner

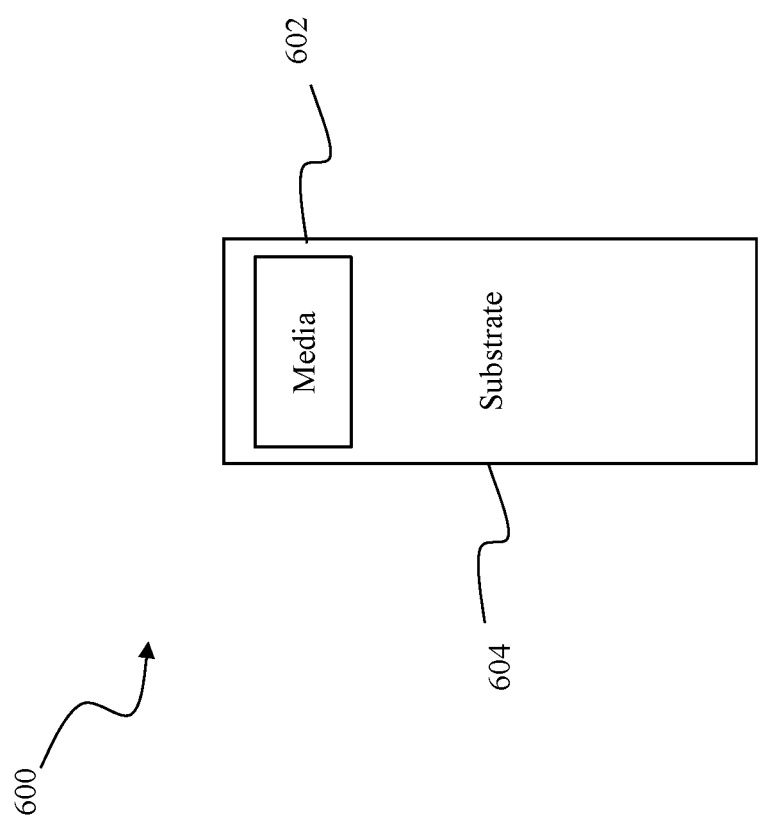

ELECTRONIC GAMING SYSTEM AND METHOD OF PROVIDING PROGRESSIVE JACKPOT PLAY

CROSS-REFERENCE TO RELATED APPLICATIONS

This application is a continuation of and claims priority to U.S. patent application Ser. No. 15/237,276, filed Aug. 15, 2016, all of which is incorporated by reference in its entirety.

TECHNICAL FIELD

The embodiments described herein relate generally to electronic gaming systems and methods that enable progressive jackpot play on electronic gaming machines that do not include a progressive jackpot component.

BACKGROUND

Many known electronic gaming machines include a progressive jackpot feature where the value of the jackpot increases by a portion of each bet wagered by a player for each game. However, at least some electronic gaming machines do not offer a progressive jackpot feature. Typically, multiple electronic gaming machines are linked together to form one large progressive jackpot that grows more quickly because one or more players playing one or more games contribute to the jackpot. Generally, in traditional casinos, every wager contributes to the progressive jackpot to grow the progressive jackpot faster and to build excitement for the players. Multiple electronic gaming machines may be linked across a casino floor, between multiple casinos, and/or over the Internet for online gaming. Progressive jackpots increase player interest and entertainment by enabling players to win a large jackpot payout in addition to the base game payout associated with the electronic gaming machine.

Generally, in traditional casinos, to qualify to win the progressive jackpot, a player must wager at least a predetermined number of credits, i.e., a qualifying bet, that is typically higher than a minimum number of credits required to play the game, i.e., a minimum bet. For many progressive jackpots, the qualifying wager is a maximum bet for a given game. Generally, all wagers contribute to the progressive jackpot. Accordingly, having a progressive jackpot feature may increase revenue for a gaming machine because players wager more credits to qualify for the progressive jackpot. For players that prefer the particular game offered by a non-progressive electronic gaming machine, there may be a decrease in potential revenue earned by the non-progressive electronic gaming machine, because the minimum wager does not qualify for the progressive jackpot that is larger than the minimum wager to play the game.

BRIEF DESCRIPTION

In one aspect, a gaming system is provided, including a jackpot server and a gaming server. The jackpot server is configured to accumulate respective contributions from a plurality of gaming client devices into a progressive jackpot. The gaming server is configured to present a plurality of wagering games to a player on a gaming client device. The plurality of wagering games include a first wagering game having a progressive jackpot component, and a second wagering game not having a progressive jackpot component. The gaming server receives a jackpot token presented by the player, the jackpot token including a token identification associated with the player and a progressive jackpot identification correlating to a token progressive jackpot. A wager is received from the player for the second wagering game and the gaming server conducts the second wagering game such that the player participates in the token progressive jackpot. The gaming server transmits a message to the jackpot server, the message including a portion of the wager as a contribution to the token progressive jackpot and an outcome of the second wagering game.

In another aspect, a method of playing a wagering game using a gaming system is provided. The method includes accumulating, by a jackpot server, respective contributions from a plurality of gaming client devices into a progressive jackpot. The method also includes presenting, by a gaming server communicatively coupled to the jackpot server, a plurality of wagering games to a player on a gaming client device. The plurality of wagering games include a first wagering game having a progressive jackpot component, and a second wagering game not having a progressive jackpot component. The method further includes receiving, by the gaming server, a jackpot token presented by the player using the gaming client device. The jackpot token includes a token identification associated with the player and a progressive jackpot identification correlating to a token progressive jackpot. The method also includes receiving, by the gaming server, a wager from the player for the second wagering game, and conducting the second wagering game such that the player participates in the token progressive jackpot. The method further includes transmitting, by the gaming server, a message to the jackpot server, the message including a portion of the wager as a contribution to the token progressive jackpot and an outcome of the second wagering game.

In yet another aspect, a token for use in a gaming system that conducts a wagering game is provided. The token includes a media and a substrate having a first surface configured to receive the media. The media includes a token identification associated with a player and the token, and a token progressive jackpot identification corresponding to a progressive jackpot in which the player optionally participates. The substrate is configured to deliver the media to the gaming system, whereupon the player participates in the token progressive jackpot through a wager and the wagering game.

BRIEF DESCRIPTION OF THE DRAWINGS

The embodiments described herein may be better understood by referring to the following description in conjunction with the accompanying drawings.

FIG. 6 is a block diagram of an exemplary jackpot token.

DETAILED DESCRIPTION

Figure 1:
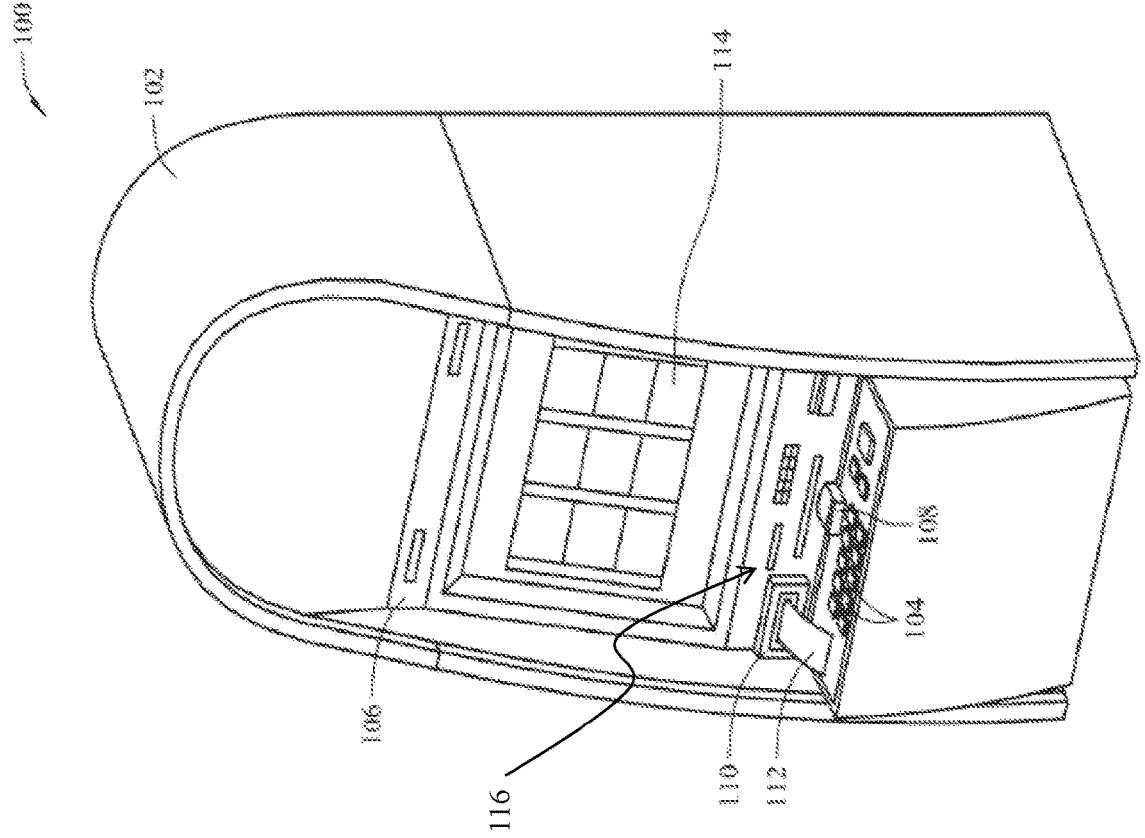
FIG. 1 is a schematic diagram of an exemplary electronic gaming machine.

According to embodiments of the invention, there is provided a gaming system in which a gaming server enables progressive jackpot play by a player for at least one wagering game that does not include an associated progressive jackpot component. A jackpot token is presented by the player using a gaming client device that provides the player an opportunity to select a particular non-progressive jackpot game and play the selected game for a token progressive jackpot for a defined period of time. The token progressive jackpot is controlled by a jackpot server of the gaming system and is associated only with games in which a player has presented a jackpot token and placed a wager having a value of at least the qualifying bet for the token progressive jackpot. In some embodiments, the qualifying bet ranges from a minimum bet for the wagering game to a maximum bet for the wagering game.

The token progressive jackpot enables players to participate in a progressive jackpot on a wagering game the player chooses. The token progressive jackpot may be enabled by any player who plays a jackpot token on an eligible wagering game, such as any wagering game without an existing progressive jackpot component. In certain embodiments, the token progressive jackpot can only be added to games that do not already include a progressive jackpot component. In alternative embodiments, the token progressive jackpot can be added to games that do include a progressive jackpot component, but the player elects to participate in the token progressive jackpot in addition to the existing progressive jackpot or in place of the existing progressive jackpot.

In some embodiments, only wagers of at least the qualifying bet contribute to the token progressive jackpot. For example, in embodiments where the casino is a virtual casino in which non-monetary currency, or virtual currency, is used in wagering, the quantity of players, i.e., the player base, may be an order-of-magnitude greater than a traditional, brick-and-mortar, casino. In such embodiments, progressive jackpots grow more quickly and may be awarded more quickly. The token progressive jackpot receives contributions from any wagering game on which a player elects to redeem a jackpot token, thus broadening the player base even further than a progressive jackpot for one or two particular wagering games. Moreover, in certain embodiments, wagering games in virtual casinos utilize a wider range of wager denominations due to their use of non-monetary currency. For example, a wagering game in a virtual casino may have a minimum wager of 6,000 credits, a qualifying wager of 200,000 credits, and a maximum wager of 12,000,000 credits. Conversely, a traditional casino utilizing monetary currency may have a minimum wager of 1 credit and a maximum wager of 3 credits and a qualifying wager of 3 credits, where one credit corresponds to one dollar.

In certain embodiments, wagers of a value below the qualifying bet still contribute to the token progressive jackpot. In such embodiments, a player placing such a wager may only be eligible for a fraction of the total token progressive jackpot. For example, for wagers valuing between the minimum bet for the game and the qualifying bet for the token progressive jackpot, the fraction of the token progressive jackpot available to win scales proportionally. In a game having a minimum bet of 5 credits, a token progressive jackpot having a qualifying bet of 9 credits, and a linear scaling of the token progressive jackpot available to win, a wager of 5 credits may qualify the player to win 20% of the token progressive jackpot, a wager of 6 credits may qualify the player to win 40% of the token progressive jackpot, a wager of 7 credits may qualify the player to win 60% of the token progressive jackpot, a wager of 8 credits may qualify the player to win 80% of the token progressive jackpot, and a wager of 9 credits qualifies the player to win the entire token progressive jackpot. In alternative embodiments, the scaling of the token progressive jackpot may be non-linear to reward higher wager values. For example, in a game having a minimum bet of 5 credits, a token progressive jackpot having a qualifying bet of 9 credits, and a non-linear scaling of the token progressive jackpot available to win, a wager of 5 credits may qualify the player to win 5% of the token progressive jackpot, a wager of 6 credits may qualify the player to win 15% of the token progressive jackpot, a wager of 7 credits may qualify the player to win 35% of the token progressive jackpot, a wager of 8 credits may qualify the player to win 65% of the token progressive jackpot, and a wager of 9 credits qualifies the player to win the entire token progressive jackpot Exemplary technical effects of the systems, methods, and apparatus described herein include at least one of: (a) configuring a gaming system to provide a progressive jackpot for non-progressive jackpot games; (b) providing a jackpot token to control the number of attempts available to players to play for the progressive jackpot for the non-progressive jackpot games; (c) increasing revenue for non-progressive jackpot games by enabling progressive jackpot play that requires a larger wager than a minimum wager for the game; and (d) increasing player interest and entertainment in non-progressive jackpot games.

FIG. 1 is a schematic diagram of an exemplary gaming machine 100. Gaming machine 100 may be any type of gaming machine, and may include, without limitation, different structures than those shown in FIG. 1, such as, for example, a personal computer, tablet computer, smart phone, personal digital assistant (PDA), cellular phone, and any other network-enabled device. Moreover, gaming machine 100 may employ different methods of operation than those described below.

In the exemplary embodiment, gaming machine 100 includes a cabinet 102 that houses a plurality of components, such as a gaming machine controller, peripheral devices, displays, and/or player interaction devices. For example, in an exemplary embodiment, gaming machine 100 includes a plurality of user interfaces, or input devices, such as switches and/or buttons 104 that are coupled to a front 106 of cabinet 102. Buttons 104 may be used to start play of a primary or secondary game. One button 104 may be a "Bet One" button that enables the player to place a bet or to increase a bet. Another button 104 may be a "Bet Max" button that enables the player to bet a maximum permitted wager. Yet another button 104 may be a "Cash Out" button that enables the player to receive a cash payment or other suitable form of payment, such as a ticket or voucher that corresponds to a number of remaining credits. User interfaces, in certain embodiments, include one or more touch screens as user interfaces.

In the exemplary embodiment, gaming machine 100 also includes a credit input device 116. Credit input device 116 may include a coin acceptor 108 for accepting coins and/or tokens, a bill validator 110 for accepting and/or validating bills, coupons, and/or ticket vouchers 112. Bill validator 110 may also be capable of printing tickets 112. Furthermore, in some embodiments, credit input device 116 includes a card reader or a validator for use with credit cards, debit cards, identification cards, and/or smart cards. Cards accepted by the card reader or validator may include a magnetic strip and/or a preprogrammed microchip that includes a player's identification, credit totals, and any other relevant information that may be used. In certain embodiments, credit input device 116 may include a credit input module that interfaces with a server to accept credit and wagers.

Moreover, in the exemplary embodiment, gaming machine 100 includes one or more displays 114. Displays 114 are mounted to cabinet 102, and may include a primary display for displaying a primary game and a secondary display for displaying a secondary or bonus game. Displays 114 may be further configured to display credit balances, wager amounts, cumulative wagering information, and payout amounts. Displays 114 may include, without limitation, a plasma display, a liquid crystal display (LCD), a display based on light emitting diodes (LEDs), organic light emitting diodes (OLEDs), polymer light emitting diodes (PLEDs), and/or surface-conduction electron emitters (SEDs), a speaker, an alarm, and/or any other device capable of presenting information to a user.

Figure 2:
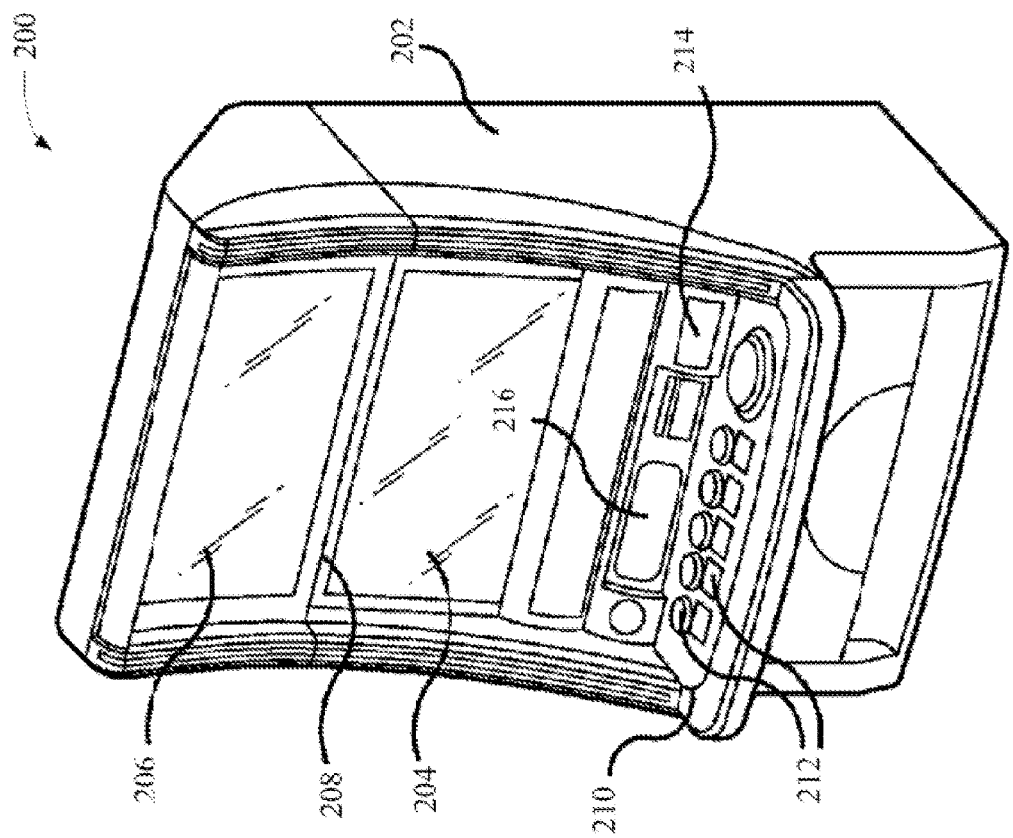
FIG. 2 is a schematic diagram of another exemplary electronic gaming machine.

With reference now to FIG. 2, another exemplary gaming machine 200 is shown. Gaming machine 200 includes a cabinet 202 mounting a main video display 204 shown as a flat screen LCD, plasma, or touch screen display. Above main video display 204 is a secondary video display 206, which likewise is a flat screen LCD or plasma display. In alternative embodiments, one or more of main video display 204 and secondary video display 206 may include a curved display. A mounting bezel 208 divides main display 204 from secondary display 206. A player interface, shown as a button panel 210, mounts a plurality of input buttons 212 through which a player controls an operation of a game. Below main video display 204 is an interface module 214 for interfacing with gaming machine 200, and a system interface display 216 for displaying system provided information (e.g., casino wide information and player points/comp data) to a player.

Figure 3:
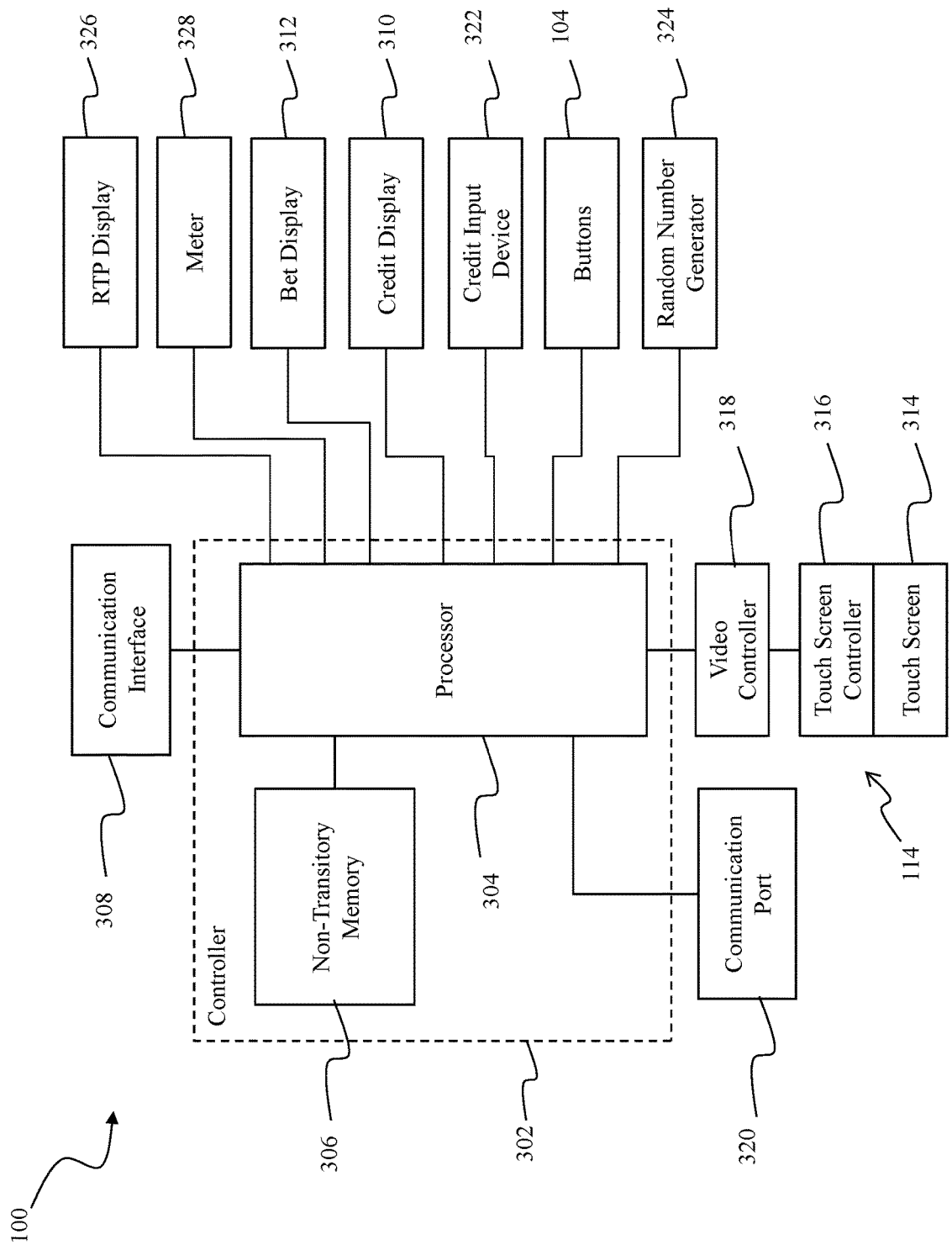
FIG. 3 is an exemplary block circuit diagram that may be used with the gaming machine shown in FIG. 1.

FIG. 3 is a schematic block diagram of gaming machine 100. In the exemplary embodiment, gaming machine 100 includes a gaming machine controller 302 having a processor 304 communicatively coupled to a non-transitory memory 306. Moreover, in the exemplary embodiment, processor 304 and non-transitory memory 306 reside within cabinet 102 (shown in FIG. 1) and may be collectively referred to herein as a "computer" or "controller." Gaming machine 100 is configurable and/or programmable to perform one or more operations described herein by programming processor 304. For example, processor 304 may be programmed by encoding an operation as one or more executable instructions and providing the executable instructions in non-transitory memory 306.

Controller 302 communicates with one or more other gaming machines 100 or other suitable devices via a communication interface 308. Communication interface 308 may operate as an input device (e.g., by receiving data from another device) and/or as an output device (e.g., by transmitting data to another device). Processor 304 may be a microprocessor, a microcontroller-based platform, a suitable integrated circuit, and/or one or more application-specific integrated circuits (ASICs). However, the above examples are exemplary only, and thus are not intended to limit in any way the definition and/or meaning of the term "processor." Gaming machine 100 includes a random number generator 324. In certain embodiments, random number generator 324 is integrated into controller 302 or processor 304. Random number generator 324 is configured to be secure from unauthorized access, manipulation, or compromise. Generally, an output of random number generator 324 is the basis on which game outcomes are determined by controller 302. Random number generator 324 may be implemented as a true random number generator or a pseudo-random number generator.

In certain embodiments, data and the computer-executable instructions may be stored in a cloud service, a database, or other non-transitory memory accessible by gaming machine 100. Such embodiments reduce the computational and storage burden on gaming machine 100. As such, non-transitory memory 306 may be a local and/or a remote computer storage media including memory storage devices. Moreover, non-transitory memory 306 may include one or more forms of memory. For example, non-transitory memory 306 can include random access memory (RAM), read-only memory (ROM), flash memory, and/or electrically erasable programmable read-only memory (EEPROM). In some embodiments, other suitable magnetic, optical, and/or semiconductor-based memory may be included in non-transitory memory 306 by itself or in combination.

When games are implemented in an online environment, at least a portion of the game software is stored in a remote game server, or in a cloud computing service. Game transactions such as adding money to the game, i.e., cash in, and withdrawing money from the game, i.e., cash out, are substituted by implementing electronic fund transfers. Each player deposits money into his online gaming account via checks, debit cards, wire and the like. Once funded, the player can move a portion of the cash in his account into the game he wants to play. This process is referred to as account-based wagering. Account-based wagering is a convenient monetary transaction system for online and mobile wagering environments since the physical bill validator and ticket printer are not available. In addition to the accounting meters' separation requirement, the detection of the location where the wagering transaction take place is also required in order to enforce local gaming regulations and to properly calculate revenue, profit, and tax withholdings, for example.

Non-transitory memory 306, in certain embodiments, is a physical storage device, such as, for example, a cartridge that is removable from gaming machine 100. Further, in certain embodiments, non-transitory memory 306 includes multiple removable physical storage devices, each configured to store certain executable program modules. In alternative embodiments, non-transitory memory 306 includes multiple partitions of a single physical storage device, each partition configured to store certain executable program modules.

Gaming machine 100 includes a credit input device 322 for accepting various forms of money or credit. Credit input device 322 may include one or more of a coin acceptor, bill validator, ticket reader, or card reader, for example. In certain embodiments, credit input device 322 includes an interface to a server configured to accept credits to establish a credit balance at gaming machine 100. Gaming machine 100 further includes at least one meter 328 for tracking and recording gaming data, including, for example amounts wagered on gaming machine 100.

Gaming machine 100 includes a credit display 310 that displays a player's current number of credits, cash, account balance or the equivalent. Gaming machine 100 also includes a bet display 312 that displays a player's amount wagered. Credit display 310 and bet display 312 may be standalone displays independent of display 114, or credit display 310 and bet display 312 may be incorporated into display 114.

Moreover, in an exemplary embodiment, display 114 is controlled by controller 302. In some embodiments, display 114 includes a touch screen 314 and an associated touch screen controller 316. In such embodiments, display 114 may operate as an input device in addition to presenting information. A video controller 318 is communicatively coupled to controller 302 and touch screen controller 316 to enable a player to input game play decisions (e.g., actions on and selections of game presentation objects) into gaming machine 100 via touch screen 314. Furthermore, gaming machine 100 includes one or more communication ports 320 that enable controller 302 to communicate with external peripheral devices (not shown) such as, but not limited to, external video sources, expansion buses, other displays, a SCSI port, or a key pad.

Controller 302 conducts the electronic game and generates gaming data. Gaming data may include, for example, wagers, game outcomes, payouts, player ratings, duration of play, and time between rounds of play. For each round of play of the electronic game, controller 302 conducts the electronic game and awards a payout.

Figure 4:
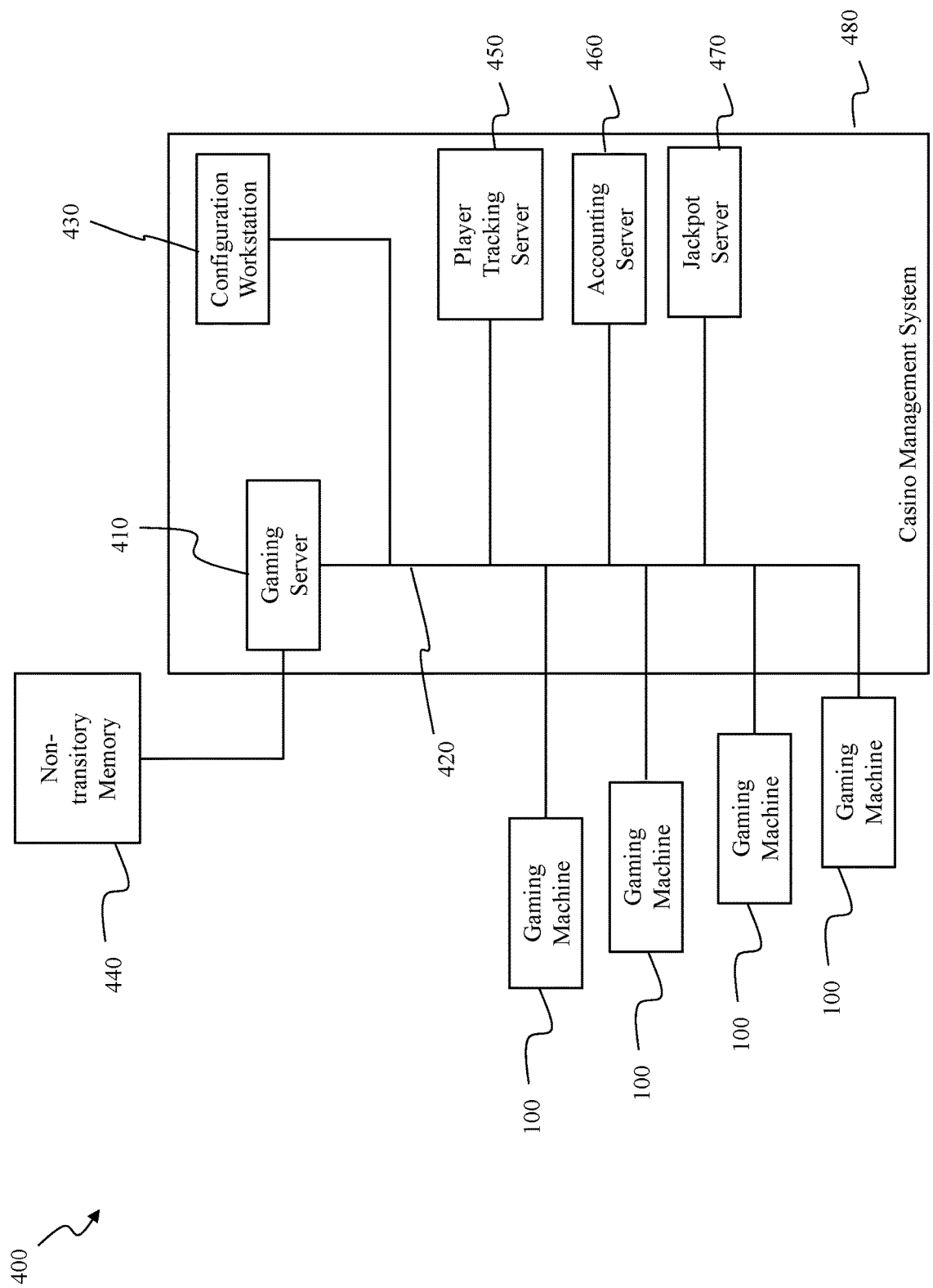
FIG. 4 is a block schematic diagram of an exemplary electronic gaming system that includes a plurality of electronic gaming machines such as the gaming machine shown in FIG. 1.

FIG. 4 is a block schematic diagram of an exemplary electronic gaming system 400 that includes a plurality of electronic gaming machines 100 (shown in FIG. 1). Each gaming machine 100 is coupled via communication interface 308 (shown in FIG. 3) to one or more servers, such as a gaming server 410, using a network 420. In certain embodiments, gaming system 400 may include a player tracking server 450, an accounting server 460, and a jackpot server 470. Gaming server 410, player tracking server 450, accounting server 460, and jackpot server 470 combine to form a casino management system 480. Gaming server 410 may have an electrical architecture similar to that of gaming machine 100. Gaming server 410 includes a processor (not shown) and a network interface, such as communication port 320 that facilitates data communication between gaming server 410, each gaming machine 100, and other components of gaming system 400. Such data is stored in, for example, a non-transitory memory 440, such as a database, that is coupled to gaming server 410. In alternative embodiments, certain server functions may be combined onto a single server system. For example, functions carried out by jackpot server 470 may be implemented on gaming server 410, thus combining jackpot server 470 and gaming server 410 into one server system, i.e., gaming server 410.

In a thick client embodiment, game server 410 of gaming system 400 implements part of the game played by a player using a gaming machine 100, and gaming machine 100 implements part of the game. With this embodiment, as both the game server and the gaming machine implement part of the game, they collectively provide a game controller. Typically, if the gaming system enables players to participate in a Jackpot game, jackpot server 470 will be provided to carry out the accounting for the Jackpot game.

In a thin client embodiment, game server 410 implements most or all of the game played by a player using a gaming client device, such as gaming machine 100, where gaming machine 100 essentially provides only the player interface. With this embodiment, game server 410 provides the game controller. Gaming machine 100 receives player instructions, passes these to game server 410, which then processes them and returns game play outcomes to gaming machine 100 for display. In a thin client embodiment, gaming machines 100 may be computer terminals, such as PCs, tablets, PDAs, laptops, or smart phones running software that provides a player interface operable using standard computer input and output components.

In certain thin client embodiments, many gaming client devices connect to game server 410 over network 420; however, network 420 is not coupled to a traditional brick-and-mortar casino where wagers are placed in monetary currency. Rather, network 420 defines a virtual casino in which non-monetary currency, or virtual currency, is used. In such embodiments, remote gaming client devices cannot participate in games conducted in a traditional casino. Rather, network 420 defines an on-line casino environment in which virtual currency is utilized for wagers and payouts. In such embodiments, a player purchases virtual currency for play in the multiple wagering games provided by game server 410. The virtual currency is not redeemable for monetary currency, and any winnings accumulated by the player are only usable within the on-line casino environment for further play. In certain such embodiments, game server 410 may implement the functionality typically carried out on player tracking server 450, accounting server 460, and jackpot server 470.

Casino management system 480 includes a configuration workstation 430 coupled to server 410 and gaming machines 100 through network 420. In one embodiment, one or more gaming machines 100 may be remote gaming machines that access a casino via network 420. As such, a player is able to participate in a game of chance on a remote gaming machine. In such an embodiment, it will be understood that a player operating a remote gaming machine has virtual access to any casino coupled to network 420 and associated with gaming server 410. Gaming machines 100 may also be a personal computers coupled to the Internet via a virtual private network such that a player may participate in a game of chance, remotely. In other embodiments, the player may use a cell phone or other mobile devices (e.g., tablets, PDAs, laptops, and the like) coupled to a wired or wireless communication network to establish a connection with a particular casino. Moreover, gaming machines 100 may be terminal-based machines, wherein the actual games, including random number generation and/or outcome determination, are performed at gaming server 410. In such an embodiment, gaming machines 100 display results of a game via display 114 (shown in FIGS. 1 and 3).

In one embodiment, gaming server 410 performs a plurality of functions including, game outcome generation, player tracking functions, and/or accounting functions, to name a few. For example, gaming server 410 may track data of players using gaming machines 100. For example, gaming server 410 can store physical characteristics of players, such as, but not limited to, a gender of a player and an age of a player. Gaming server 410 can also track and store other data related to the players using player tracking identification, such as a player card. For example, gaming server 410 can store information about a player, such as loyalty points, player address, phone number, and/or any information that may be retrieved and transmitted to gaming machines 100. In some embodiments, gaming server 410 stores and tracks information such as, but not limited to, an average amount of a wager played at gaming machines 100, any funds (virtual or monetary) a player may have in an account, as well as data relating to reportable events. However, in alternative embodiments, gaming system 400 may include a plurality of servers that separately perform these functions and/or any suitable function for use in a network-based gaming system.

Casino management system 480 includes at least one processor among gaming server 410, configuration workstation 430, player tracking server 450, accounting server 460, and jackpot server 470. Casino management system 480 is coupled to gaming machines 100 over network 420. Casino management system 480 is configured to receive gaming data from gaming machines 100 as each of gaming machines 100 conducts various rounds of play of one or more electronic games.

Gaming server 410 is configured to present a plurality of wagering games to a player on gaming machine 100. The wagering games include at least some wagering games that include a progressive jackpot component, and at least some other wagering games that do not include a progressive jackpot component. In wagering games that do not have a progressive jackpot component, a player may make a wager that does not contribute to token progressive jackpot and the player is ineligible to win the token progressive jackpot. The player is only eligible to win the prizes awarded in that base wagering game.

When gaming server 410 receives a jackpot token from the player, through gaming machine 100, the token progressive jackpot is added to the base wagering game. The jackpot token includes a token identification associated with the player and a progressive jackpot identification correlating to a token progressive jackpot. The token identification identifies to gaming server 410 that the jackpot token is associated with a particular player or player account, a length of time for which the player may play for the token progressive jackpot, and an expiration date/time for the jackpot token.

The token progressive jackpot is a progressive jackpot controlled by jackpot server 470 that is not associated with any particular game or gaming machine. Rather, the jackpot token is redeemable wagering games not having a progressive jackpot component. This enables the player to play a desired game with a chance to win a progressive jackpot that does not otherwise have a progressive jackpot associated with it. Because jackpot server 470 is centrally maintained on network 420, jackpot tokens may be issued to a plurality of players and may be redeemed for any game not having a progressive jackpot.

In one embodiment, upon receiving the jackpot token, gaming server 410 displays a plurality of wagering games not having a progressive jackpot component that are available to the player for application of the jackpot token. Gaming server 410 may also continuously retrieve a current token progressive jackpot amount and display it to the player. Gaming server 410 then receives a player selection of which of the plurality of second wagering games the player desires to apply the jackpot token.

The player selects a particular second wagering game to play for the token progressive jackpot. Gaming server 410 is configured to receive a wager from the player for the second wagering game. The wager is received by game machine 100 from the player using a credit input mechanism or is subtracted from a credit balance associated with the player's account. A portion of the wager is contributed toward the token progressive jackpot. In the exemplary embodiment, the wager must meet or exceed a predetermined qualifying wager amount to enable the player to qualify for the token progressive jackpot. The predetermined qualifying wager amount exceeds a minimum wager amount required to play the game. In this case, the jackpot token's function is to enable progressive jackpot play on a non-progressive jackpot gaming machine.

In another embodiment, the jackpot token serves as a qualifying wager for the selected gaming machine for the defined period of time such that the player may play for the token progressive jackpot by wagering the minimum wager required to play the game.

Gaming server 410 is configured to conduct the second wagering game such that the player participates in the progressive jackpot. Conducting the second wagering game includes determining an outcome of the second wagering game. Gaming server 410 generates gaming data for the second wagering game. The gaming data may include, for example, wagers, game outcomes, payouts, player ratings, duration of play, and/or time between rounds of play. For each round of play of the electronic game, gaming server 410 conducts the electronic game and awards a payout.

Gaming server 410 is configured to transmit a message to jackpot server 470, the message including the portion of the wager as a contribution to the token progressive jackpot and the outcome of the second wagering game. Jackpot server 470 determines whether the token progressive jackpot is to be paid out based on the outcome, and if so, instructs gaming server 410 of the amount of the payout.

Figure 5:
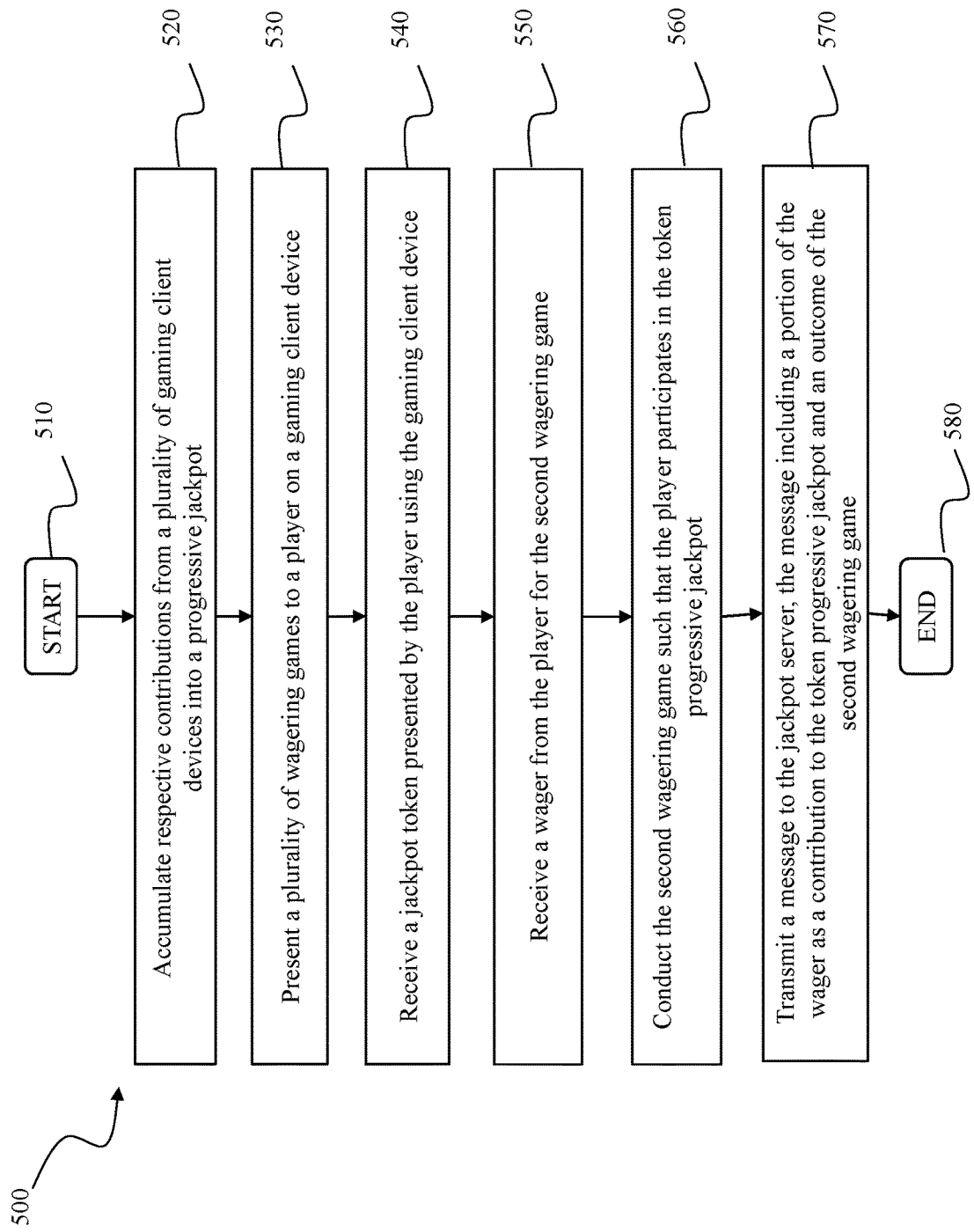
FIG. 5 is a flow diagram of an exemplary method of playing a wagering game using an exemplary gaming system.

FIG. 5 is a flow diagram of an exemplary method 500 of playing a wagering game using a gaming system, such as electronic gaming system 400 (shown in FIG. 4). Method 500 begins at a start step 510. At an accumulating step 520, respective contributions are accumulated into a progressive jackpot by a jackpot server from a plurality of gaming client devices. A plurality of wagering games is presented to a player on a gaming client device by a gaming server communicatively coupled to the jackpot server at a presenting step 530. The plurality of wagering games include a first wagering game having a progressive jackpot component, and a second wagering game not having a progressive jackpot component.

At a token receiving step 540, the gaming server receives a jackpot token presented by the player using the gaming client device. The jackpot token includes a token identification associated with the player and a progressive jackpot identification correlating to a token progressive jackpot. In certain embodiments, token receiving step 540 may include identifying, by the gaming server, at least one of a particular player account associated with the jackpot token, a length of time for which the player may play for the token progressive jackpot, and an expiration of the jackpot token.

A wager is received by the gaming server from the player for the second wagering game at a wager receiving step 550. The gaming server then conducts the second wagering game such that the player participates in the token progressive jackpot at a conducting step 560.

At a transmitting step 570, the gaming server transmits a message to the jackpot server, the message including a portion of the wager as a contribution to the token progressive jackpot and an outcome of the second wagering game.

In certain embodiments, method 500 may further include generating, by the jackpot server, the token progressive jackpot, and associating the token progressive jackpot only with the second wagering game or any other wagering game not having a progressive jackpot component in which a jackpot token has been redeemed.

In certain embodiments, method 500 may further include receiving, by the jackpot server, the message from the gaming server, determining whether the token progressive jackpot is to be paid out based on the outcome of the second wagering game, and when a token progressive jackpot payout is to be made, transmitting a message instructing the gaming server of an amount of the token progressive jackpot payout to pay to the player.

In certain embodiments, the first wagering game includes a plurality of first wagering games, and the second wagering game includes a plurality of second wagering games, and the method 500 further includes continuously retrieving, by the gaming server, a current token progressive jackpot amount from the jackpot server, and displaying the current token progressive jackpot to the player via the gaming client device. The wager receiving step 550 may further include receiving the wager from the player using a credit input mechanism of the gaming client device, and subtracting the wager from a credit balance associated with the player, the credit balance stored on a player tracking server of the gaming system.

FIG. 6 is a block diagram of an exemplary jackpot token 600. The jackpot token includes a media 602 and a substrate 604 having a first surface configured to receive media 602.

The media 602 includes a token identification associated with a player and the token, and a token progressive jackpot identification corresponding to a progressive jackpot in which the player optionally participates. The media 602 may include printed text, such as a textual code. The media 602 may include data stored on a magnetic strip or a non-volatile non-transitory memory, such as a smart chip, for example.

Substrate 604 is configured to deliver the media to the gaming system, whereupon the player participates in the token progressive jackpot through a wager and the wagering game. Substrate 604 may include a printable ticket or voucher, a disposable card, or a player card. For example, a player may present the jackpot token to gaming server 410 in the form of a ticket or voucher via a credit input mechanism. In alternative embodiments, a player may type a code into a player interface. In certain embodiments, data for the jackpot token 600 may be stored by player tracking server 450 on a player account or a player card such that the player may scan or touch the card to redeem the jackpot token.

In an alternative embodiment, jackpot token 600 is an electronic token. In such an embodiments, media 602 is an electronic media, such as an email or text message, for example. Media 602 includes, in the electronic media, the token identification, progressive jackpot identification, and any other data relevant to the progressive jackpot, such as, for example, current jackpot size, the date of the last jackpot award, or the size of the last jackpot awarded.

The systems and methods described herein are not limited to the specific embodiments described herein but, rather, operations of the methods and/or components of the system and/or apparatus may be utilized independently and separately from other operations and/or components described herein. Further, the described operations and/or components may also be defined in, or used in combination with, other systems, methods, and/or apparatus, and are not limited to practice with only the systems, methods, and storage media as described herein.

A computer, controller, or server, such as those described herein, includes at least one processor or processing unit and a system memory. The computer, controller, or server typically has at least some form of computer readable non-transitory media. As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit, and other programmable circuits "configured to" carry out programmable instructions, and these terms are used interchangeably herein. In the embodiments described herein, memory may include, but is not limited to, a computer-readable medium or computer storage media, volatile and nonvolatile media, removable and non-removable media implemented in any method or technology for storage of information such as computer readable instructions, data structures, program modules, or other data. Such memory includes a random access memory (RAM), computer storage media, communication media, and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Although the present disclosure is described in connection with an exemplary gaming system environment, embodiments of the present disclosure are operational with numerous other general purpose or special purpose gaming system environments or configurations. The gaming system environment is not intended to suggest any limitation as to the scope of use or functionality of any aspect of the disclosure. Moreover, the gaming system environment should not be interpreted as having any dependency or requirement relating to any one or combination of components illustrated in the exemplary operating environment.

Embodiments of the present disclosure may be described in the general context of computer-executable instructions, such as program components or modules, executed by one or more computers or other devices. Aspects of the present disclosure may be implemented with any number and organization of components or modules. For example, aspects of the present disclosure are not limited to the specific computer-executable instructions or the specific components or modules illustrated in the figures and described herein. Alternative embodiments of the present disclosure may include different computer-executable instructions or components having more or less functionality than illustrated and described herein.

The order of execution or performance of the operations in the embodiments of the present disclosure illustrated and described herein is not essential, unless otherwise specified. That is, the operations may be performed in any order, unless otherwise specified, and embodiments of the present disclosure may include additional or fewer operations than those disclosed herein. For example, it is contemplated that executing or performing a particular operation before, contemporaneously with, or after another operation is within the scope of aspects of the present disclosure.

When introducing elements of aspects of the present disclosure or embodiments thereof, the articles "a," "an," "the," and "said" are intended to mean that there are one or more of the elements. The terms "comprising," including," and "having" are intended to be inclusive and mean that there may be additional elements other than the listed elements.

The present disclosure uses examples to disclose the best mode, and also to enable any person skilled in the art to practice the claimed subject matter, including making and using any devices or systems and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A gaming system, said gaming system comprising:
   a server configured to accumulate respective contributions from a plurality of gaming client devices into a token progressive; and
   a gaming server in communication with the server and comprising at least one processor, wherein the at least one processor is configured to, in conjunction with a gaming client device:
      present an electronic game to a player on the gaming client device of the plurality of gaming client devices, the electronic game not having a progressive component;
      receive data from a token, the token comprising a storage media storing the data, the data including a token identification associated with the player and a progressive identification associated with the token progressive, wherein the token progressive is associated with a progressive jackpot amount;
      receive an input for the electronic game including an input amount;
      in response to receiving the data from the token and the input amount, link the electronic game with the token progressive;
      determine a current progressive jackpot amount associated with the token progressive;
      cause display, on the gaming client device, of the current progressive jackpot amount associated with the token progressive;
      conduct the electronic game such that the electronic game participates in the token progressive by:
         applying the input amount to a play of the electronic game;
         determining a percentage of the current progressive jackpot amount eligible to be presented for the play of the electronic game based upon the input amount; and
         after the input amount is applied to the play of the electronic game, applying a portion of the input amount to the token progressive.

2. The gaming system of claim 1, wherein all of the input amount is initially applied to play of the electronic game, and wherein the gaming server is further configured to:
   identify a predetermined portion of the input amount to later be applied to the token progressive, after all of the input amount is initially applied to play of the electronic game; and
   transmit a message to said server, the message including an outcome of the electronic game and the predetermined portion of the input amount which is to be credited as a contribution to the token progressive.

3. The gaming system of claim 2, wherein in response to receiving the message from said gaming server, said server is configured to:
   determine, based upon the outcome of the electronic game, to present an output including at least a portion of the token progressive; and
   transmit a message instructing said gaming server of an amount of the token progressive to be outputted at the gaming client device.

4. The gaming system of claim 1, wherein the token identification identifies at least one of a particular player account, a length of time for which the player may play for the token progressive, and an expiration of the token.

5. The gaming system of claim 1, wherein the gaming server is further configured to present a plurality of first electronic games including progressive components, and a second plurality of electronic games not including progressive components, the second plurality of electronic games including the electronic game.

6. The gaming system of claim 5, wherein upon receiving the data from the token, said gaming server is configured to cause display of the second plurality of electronic games not including progressive components that are available to the player for application of the token.

7. The gaming system of claim 1, wherein said gaming server is further configured to continuously retrieve the current progressive jackpot amount associated with the token progressive.

8. The gaming system of claim 1, wherein to receive the input from the player, said gaming server is further configured to at least one of receive the input from the player using a credit input mechanism and subtract the input amount from a credit balance associated with the player.

9. The gaming system of claim 1, wherein the received input amount must meet or exceed a predetermined qualifying input amount to qualify to win the token progressive, the predetermined qualifying input amount being greater than a minimum input amount for the gaming client device.

10. The gaming system of claim 1, wherein the token serves as a qualifying input to qualify to win the token progressive, and the received input amount must meet or exceed a minimum input amount for the gaming client device.

11. The gaming system of claim 1, wherein the plurality of gaming client devices includes at least one of an electronic gaming machine in a casino, a remote gaming machine accessing the casino via a network, a remote gaming machine having virtual access to any casino coupled to the network and associated with said gaming server, and a personal computer or mobile device coupled to the Internet via a virtual private network such that the player may participate in the electronic game remotely.

12. A method of playing an electronic game using a gaming system including a server in communication with a gaming server comprising at least one processor, said method comprising:

presenting, by the at least one processor, an electronic game to a player on a gaming client device, the electronic game not having a progressive component;

receiving, by the at least one processor, data from a token, the token comprising a storage media storing the data, the data including a token identification associated with the player and a progressive identification associated with the token progressive, wherein the token progressive is associated with a progressive jackpot amount;

receiving, by the at least one processor, an input for the electronic game including an input amount;

in response to receiving the data from the token and the input amount, linking, by the at least one processor, the electronic game with the token progressive;

determining, by the at least one processor, a current progressive jackpot amount associated with the token progressive;

causing display, by the at least one processor on the gaming client device, of the current progressive jackpot amount associated with the token progressive;

conducting, by the at least one processor, the electronic game such that the electronic game participates in the token progressive by:

applying, by the at least one processor, the input amount to a play of the electronic game;

determining, by the at least one processor, a percentage of the current progressive jackpot amount eligible to be presented for the play of the electronic game based upon the input amount; and applying, by the at least one processor and after the input amount is applied to the play of the electronic game, a portion of the input amount to the token progressive.

13. The method of claim 12, wherein all of the input amount is initially applied to play of the electronic game, the method further comprising:

identifying a predetermined portion of the input amount to later be applied to the token progressive, after all of the input amount is initially applied to play of the electronic game; and transmitting a message to said server, the message including an outcome of the electronic game and the predetermined portion of the input amount which is to be credited as a contribution to the token progressive.

14. The method of claim 13, further comprising:

determining, based upon the outcome of the electronic game, to present an output including at least a portion of the token progressive; and transmitting a message instructing said gaming server of an amount of the token progressive to be outputted at the gaming client device.

15. The method of claim 12, further comprising continuously retrieving the current progressive jackpot amount associated with the token progressive.

16. The method of claim 12, further comprising, in response to receiving the data from the token, causing display of a plurality of electronic games not including progressive components that are available for application of the token, the plurality of electronic games including the electronic game.

17. The method of claim 12, wherein receiving the input comprises at least one of:

receiving the input from the player using a credit input mechanism of the gaming client device; and subtracting the input amount from a credit balance associated with the player.

18. A non-transitory computer-readable storage medium having instructions stored thereon that, in response to execution by a processor, cause the processor to:

present an electronic game to a player on a gaming client device of a plurality of gaming client devices, the electronic game not having a progressive component;

receive data from a token, the token comprising a storage media storing the data, the data including a token identification associated with the player and a progressive identification associated with the token progressive, wherein the token progressive is associated with a progressive jackpot amount;

receive an input for the electronic game including an input amount;

in response to receiving the data from the token and the input amount, link the electronic game with the token progressive;

determine a current progressive jackpot amount associated with the token progressive;

cause display, on the gaming client device, of the current progressive jackpot amount associated with the token progressive;

conduct the electronic game such that the electronic game participates in the token progressive by:

applying the input amount to a play of the electronic game;

determining a percentage of the current progressive jackpot amount eligible to be presented for the play of the electronic game based upon the input amount; and after the input amount is applied to the play of the electronic game, applying a portion of the input amount to the token progressive.

19. The non-transitory computer-readable storage medium of claim 18, wherein all of the input amount is initially applied to play of the electronic game, and wherein the instructions further cause the processor to:

identify a predetermined portion of the input amount to later be applied to the token progressive, after all of the input amount is initially applied to play of the electronic game; and transmit a message to a jackpot server, the message including an outcome of the electronic game and the predetermined portion of the input amount which is to be credited as a contribution to the token progressive.

20. The non-transitory computer-readable storage medium of claim 18, wherein the instructions further cause the processor to receive the data from the token, the data including a token identification, wherein the token identification identifies at least one of a particular player account, a length of time for which the player may play for the token progressive, and an expiration of the token.

* * * * *